US010646826B2

(12) United States Patent
Corma Canós et al.

(10) Patent No.: US 10,646,826 B2
(45) Date of Patent: May 12, 2020

(54) METHOD FOR THE DIRECT SYNTHESIS OF CU-CONTAINING SILICOALUMINATE MATERIAL WITH THE AEI ZEOLITE STRUCTURE, AND THE CATALYTIC APPLICATIONS THEREOF

(71) Applicants: Consejo Superior de Investigaciones Científicas (CSIC), Madrid (ES); Universitat Politècnica de València, Valencia (ES)

(72) Inventors: Avelino Corma Canós, Valencia (ES); Manuel Moliner Marín, Valencia (ES); Nuria Martín García, Valencia (ES)

(73) Assignees: Consejo Superior de Investigaciones Cientificas, Madrid (ES); Universitat Politècnica de València, Valencia (ES)

( * ) Notice: Subject to any disclaimer, the term of this patent is extended or adjusted under 35 U.S.C. 154(b) by 206 days.

(21) Appl. No.: 15/566,585

(22) PCT Filed: Apr. 14, 2016

(86) PCT No.: PCT/EP2016/058278
§ 371 (c)(1),
(2) Date: Oct. 13, 2017

(87) PCT Pub. No.: WO2016/166247
PCT Pub. Date: Oct. 20, 2016

(65) Prior Publication Data
US 2018/0141001 A1    May 24, 2018

(30) Foreign Application Priority Data

Apr. 16, 2015    (ES) .................................. 201530513

(51) Int. Cl.
*C01B 39/48*    (2006.01)
*B01J 29/76*    (2006.01)
(Continued)

(52) U.S. Cl.
CPC .......... *B01D 53/9418* (2013.01); *B01J 29/76* (2013.01); *B01J 35/0006* (2013.01);
(Continued)

(58) Field of Classification Search
CPC ...... C01B 39/026; C01B 39/48; B01J 29/072; B01J 29/70; B01J 29/76; F01N 3/2066; B01D 53/9418
See application file for complete search history.

(56) References Cited

U.S. PATENT DOCUMENTS 5,958,370 A * 9/1999 Zones .................... B01D 53/02
                                                                    208/111.01
9,044,744 B2 * 6/2015 Casci ................. B01D 53/9418
(Continued)

FOREIGN PATENT DOCUMENTS

EA          200601199 A1    12/2006
EA              011395 B1     2/2009
(Continued)

OTHER PUBLICATIONS

T. Sonada et al., "Synthesis of High-Silica AEI Zeolites with Enhanced Thermal Stability by Hydrothermal Conversion of FAU Zeolites, and Their Activity in the Selective Catalytic Reduction of $NO_x$ with $NH_3$." Journal of Materials Chemistry A, vol. 3, pp. 857-865, 2015.
(Continued)

*Primary Examiner* — David M Brunsman
(74) *Attorney, Agent, or Firm* — Suzannah K. Sundby, Esq.; Canady + Lortz LLP

(57) ABSTRACT

The present invention provides a new method for preparing the copper-containing silicoaluminate form of the AEI zeolite structure by means of a direct synthesis methodology. This new process involves combining a organometallic copper-complex with an additional organic molecule
(Continued)

capable of directing the crystallization of the silicoaluminate form of the AEI zeolite structure as organic structure-directing agents (OSDAs).

37 Claims, 1 Drawing Sheet

(51) Int. Cl.

| | |
|---|---|
| B01D 53/94 | (2006.01) |
| C01B 39/02 | (2006.01) |
| B01J 35/00 | (2006.01) |
| B01J 37/00 | (2006.01) |
| B01J 37/04 | (2006.01) |
| B01J 37/10 | (2006.01) |
| C07C 29/00 | (2006.01) |
| F01N 3/20 | (2006.01) |

(52) U.S. Cl.
CPC ......... *B01J 37/009* (2013.01); *B01J 37/0018* (2013.01); *B01J 37/04* (2013.01); *B01J 37/10* (2013.01); *C01B 39/026* (2013.01); *C01B 39/48* (2013.01); *C07C 29/00* (2013.01); *F01N 3/2066* (2013.01); *B01D 2255/1021* (2013.01); *B01D 2255/1023* (2013.01); *B01D 2255/50* (2013.01); *F01N 2370/04* (2013.01)

(56) References Cited

U.S. PATENT DOCUMENTS

| 9,480,976 B2* | 11/2016 | Rivas-Cardona ........................... B01D 53/9418 |
|---|---|---|
| 10,035,141 B2* | 7/2018 | Sano .................. B01D 53/8628 |
| 2013/0159828 A1 | 6/2013 | Bangalore et al. |
| 2014/0271426 A1 | 9/2014 | Casci et al. |

FOREIGN PATENT DOCUMENTS

| EP | 2517778 A1 | 10/2012 |
|---|---|---|
| WO | WO 2005/063624 A1 | 7/2005 |
| WO | WO 2013/159825 A1 | 10/2013 |
| WO | WO 2015/005369 A1 | 1/2015 |
| WO | WO 2015/084834 A1 | 6/2015 |

OTHER PUBLICATIONS

T. Sonoda et al., Supplementary Information—Synthesis of High-Silica AEI Zeolite with Enhanced Thermal Stability by Hydrothermal Conversion of FAU Zeolite, and its Activity in the Selective Catalytic Reduction of $NO_x$ with $NH_3$. Supplementary Material (ESI) for Journal of Materials Chemistry A, Jun. 27, 2012.

M. Moliner et al., "Cu-SSZ-39, an Active and Hydrothermally Stable Catalyst for the Selective Catalytic Reduction of $NO_x$." Chemical Communications, vol. 48, pp. 8264-8266, 2012.

M. Moliner et al., "Cu-SSZ-39, an Active and Hydrothermally Stable Catalyst for the Selective Catalytic Reduction of $NO_x$." Electronic Supplementary Information (ESI).

R. Martinez-Franco et al., "Direct Synthesis Design of Cu-SAPO-18, a very Efficient Catalyst for the SCR of $NO_x$." Journal of Catalysis, vol. 319, pp. 36-43, 2014.

Search Report and Office Action received in RU2017139759 dated Sep. 5, 2019.

* cited by examiner

METHOD FOR THE DIRECT SYNTHESIS OF CU-CONTAINING SILICOALUMINATE MATERIAL WITH THE AEI ZEOLITE STRUCTURE, AND THE CATALYTIC APPLICATIONS THEREOF

TECHNICAL FIELD

The present invention relates to a new method for preparing the silicoaluminate form of the AEI zeolite structure, containing copper atoms introduced therein, by means of a direct synthesis methodology. This new methodology requires the combination of a copper organometallic complex and an organic molecule capable of directing the crystallisation of the AEI zeolite structure as organic co-structure-directing agents (OSDAs). The present invention also relates to the application of said Cu-containing silicoaluminate materials with the AEI zeolite structure as catalysts in the selective catalytic reduction (SCR) of $NO_x$, amongst others.

BACKGROUND

Zeolites are microporous materials formed by $TO_4$ tetrahedra (T=Si, Al, P, Ti, Ge, Sn, etc.) interconnected by oxygen atoms creating pores and cavities of uniform size and shape within the molecular range (3-15 Å).

These microporous crystalline materials may be used as catalysts in numerous chemical processes. The use of a zeolite with specific physico-chemical properties in a given chemical process is directly dependent on the nature of the reagents and products involved in the process (such as size, shape, hydrophobicity, etc.), as well as the reaction conditions. On the one hand, the nature of the reagents and products will affect the diffusion of these molecules in the pores and cavities of the zeolite and, consequently, the choice of a zeolite with a suitable pore topology for the products involved in the reaction is essential. On the other hand, the zeolite must be chemically and structurally stable under the required reaction conditions.

The formation of nitrogen oxides (NOx) during the combustion of fossil fuels has become a problem for society, since they are amongst the main air pollutants. The selective catalytic reduction (SCR) of NOx using ammonia as the reducing agent has become an efficient method for controlling said emissions (Brandenberger, et al. Catal. Rev. Sci. Eng., 2008, 50, 492).

Recently, it has been disclosed that silicoaluminates with the AEI structure and Cu atoms introduced therein present high catalytic activity and hydrothermal stability in the SCR reduction of $NO_x$ (Moliner et al. WO2013159825; Moliner et al. Chem. Commun., 2012, 2012, 48, 8264).

The AEI zeolite structure presents a tri-directional system of small pores (<4 Å) interconnected by large cavities, and also double six-membered rings (DA6) as secondary building units (Wagner, et al. J. Am. Chem. Soc., 2000, 122, 263).

The silicoaluminate form of the AEI zeolite structure can be synthesised using cyclic ammonium cations with alkyl substituents (Zones et al. U.S. Pat. No. 5,958,370; Cao et al. WO 2005/063624; Moliner et al. WO2013159825) or tetraalkylphosphonium cations (Sano et al. WO/2015/005369) as OSDAs.

In order to prepare the copper-containing silicoaluminate form of the AEI zeolite structure, the incorporation of the copper species is preferably performed by means of post-synthetic metal ion exchange processes on the previously synthesised and calcined AEI material (Moliner et al. WO2013159825; Sonoda, et al. J. Mater. Chem. A., 2015, 3, 857). When using this methodology, several steps are required to obtain the final material, including the hydrothermal synthesis of the silicoaluminate, calcination in order to eliminate the OSDA, transformation into the ammonium form, metal ion exchange and, finally, calcination, to obtain the material in the desired Cu-silicoaluminate form. All these steps contribute to increase the total cost of the material preparation process.

Therefore, the possibility of directly synthesising the material with the copper-containing silicoaluminate form of the AEI zeolite structure may considerably decrease the costs associated with the preparation thereof, since it would avoid most of the steps described above, making these directly prepared materials very attractive for industry.

DESCRIPTION OF THE INVENTION

The main object of the present invention is to provide a new method for preparing the copper-containing silicoaluminate form of the AEI zeolite structure by means of a direct synthesis methodology. This new process involves combining a copper organometallic complex with an additional organic molecule capable of directing the crystallisation of the silicoaluminate form of the AEI zeolite structure as organic structure-directing agents (OSDAs). The additional organic molecule may be, amongst others, any cyclic ammonium cation with alkyl substituents, such as N,N-dimethyl-3,5-dimethylpiperidinium.

Following this synthesis process, it is possible to synthesise the copper-containing silicoaluminate form of the AEI zeolite structure directly, thus avoiding the steps required to obtain said material by means of the traditional post-synthetic metal ion exchange processes.

The present invention also relates to the use as catalysts of the materials with the copper-containing silicoaluminate form of the AEI zeolite structure obtained according to the present methodology.

Therefore, the present invention relates to a process for the direct synthesis of the material with the copper-containing silicoaluminate form of the AEI zeolite structure with high synthesis yields, which comprises, at least, the following steps:

(i) Preparation of a mixture containing, at least, one source of water, one source of copper, one polyamine to form the Cu organometallic complex, one source of tetravalent element Y, one source of trivalent element X, one cyclic ammonium cation with alkyl substituents as the OSDA and one source of alkaline or alkaline-earth cations (A), where the synthesis mixture has the following molar composition:

$YO_2 : aX_2O_3 : b\text{OSDA} : cA : dH_2O : e\text{Cu} : f\text{ Polyamine}$ where
- a ranges between 0.001 and 0.2, preferably between 0.005 and 0.1, and, more preferably, between 0.01 and 0.07;
- b ranges between 0.01 and 2; preferably between 0.1 and 1, and, more preferably, between 0.1 and 0.6;
- c ranges between 0 and 2; preferably between 0.001 and 1, and, more preferably, between 0.01 and 0.8;
- d ranges between 1 and 200; preferably between 1 and 50, and, more preferably, between 2 and 20;
- e ranges between 0.001 and 1; preferably between 0.001 and 0.6, and, more preferably, between 0.001 and 0.5;
- f ranges between 0.001 and 1; preferably between 0.001 and 0.6, and, more preferably, between 0.001 and 0.5.

(ii) Crystallisation of the mixture obtained in (i) in a reactor.

(iii) Recovery of the crystalline material obtained in (ii).

According to the present invention, Y is a tetravalent element that may be preferably selected from Si, Sn, Ti, Ge and combinations thereof; more preferably, it is Si.

The source of Si used may be selected from silicon oxide, silicon halide, colloidal silica, fumed silica, tetraalkyl orthosilicate, silicate, silicic acid, a previously synthesised crystalline material, a previously synthesised amorphous material and combinations thereof, and, more preferably, it is a material selected from a previously synthesised crystalline material, a previously synthesised amorphous material and combinations thereof; more preferably, it is a previously synthesised crystalline material.

According to the present invention, X is a trivalent element that may be preferably selected from Al, B, Fe, In, Ga and combinations thereof; more preferably, it is Al.

The source of Al used may be selected from any aluminum salt, any hydrated aluminum oxide, any aluminum alkoxide, a previously synthesised crystalline material, a previously synthesised amorphous material and combinations thereof, and, more preferably, it is a material selected from a previously synthesised crystalline material, a previously synthesised amorphous material and combinations thereof; more preferably, it is a previously synthesised crystalline material.

According to a particular embodiment of the present invention, the crystalline material with the FAU zeolite structure may be used in (i) as the only source of Y and X, preferably silicon and aluminum, and may preferably present a Si/Al ratio greater than 7.

Therefore, according to a particular embodiment of the present invention, Y is Si and X is Al, for which reason the process for the direct synthesis of the material with the copper-containing silicoaluminate form of the AEI zeolite structure with high synthesis yields would comprise, at least, the following steps:

(i) Preparation of a mixture containing, at least, one source of water, one source of copper, one polyamine to form the Cu organometallic complex, one zeolite with the FAU crystal structure, such as zeolite Y, as the only source of silicon and aluminum, one cyclic ammonium cation with alkyl substituents as the OSDA and one source of alkaline or alkaline-earth cations (A), where the synthesis mixture has the following molar composition:

SiO$_2$:$a$Al$_2$O$_3$:$b$OSDA:$c$A:$d$H$_2$O:$e$Cu:$f$ Polyamine where
a ranges between 0.001 and 0.2, preferably between 0.005 and 0.1, and, more preferably, between 0.01 and 0.07;
b ranges between 0.01 and 2; preferably between 0.1 and 1, and, more preferably, between 0.1 and 0.6;
c ranges between 0 and 2; preferably between 0.001 and 1, and, more preferably, between 0.01 and 0.8;
d ranges between 1 and 200; preferably between 1 and 50, and, more preferably, between 2 and 20;
e ranges between 0.001 and 1; preferably between 0.001 and 0.6, and, more preferably, between 0.001 a 0.5;
f ranges between 0.001 and 1; preferably between 0.001 and 0.6, and, more preferably, between 0.001 and 0.5.

(ii) Crystallisation of the mixture obtained in (i) in a reactor.

(iii) Recovery of the crystalline material obtained in (ii).

According to the present invention, any source of Cu may be used in (i). Preferably, the source of copper may be selected from nitrate, sulfate and oxalate salts, and combinations thereof, amongst others.

According to the present invention, the mixture formed in (i) is free from any source of phosphorous.

According to a preferred embodiment of the present invention, the mixture formed in (i) may be free from any source of fluorine.

According to a preferred embodiment of the present invention, the source of alkaline or alkaline-earth cations may be any source of these elements, and may be preferably selected from a source of Na, K, and combinations thereof.

According to the present invention, the OSDA required in step (i) may be any cyclic ammonium cation with an alkyl substituent, preferably a quaternary ammonium selected from N,N-dimethyl-3,5-dimethylpiperidinium (DMDMP), N,N-diethyl-2,6-dimethylpiperidinium (DEDMP), N,N-dimethyl-2,6-dimethylpiperidinium, N-ethyl-N-methyl-2,6-dimethylpiperidinium and combinations thereof, preferably N,N-dimethyl-3,5-dimethylpiperidinium.

According to a particular embodiment, the process of the present invention may further comprise another OSDA, called co-operative OSDA, which may also be present in step (i), and may be selected from any cyclic quaternary ammonium or any other organic molecule, such as, for example, any amine or quaternary ammonium.

According to the present invention, any polyamine or mixture of different polyamines capable of forming a copper complex may be used in (i), regardless of the form (cyclic, linear, branched, etc.), and regardless of the nature of the amine (primary, secondary or tertiary). Preferably, said polyamine may be selected from tetraethylenepentamine, triethylenetetramine, 1,4,8,11-tetraazacyclotetradecane, 1,4,8,11-tetramethyl-1,4,8,11-tetraazacyclotetradecane, and combinations thereof, amongst others. Preferably, the polyamine is tetraethylenepentamine.

According to the present invention, the crystallisation process described in (ii) is preferably performed in autoclaves, under static or dynamic conditions (for example, by stirring the mixture) at a temperature selected from 100° C. and 200° C., preferably between 130° C. and 200° C., and, more preferably, between 130° C. and 175° C.; with a crystallisation time that may range between 6 hours and 50 days, preferably between 1 and 20 days, and, more preferably, between 2 and 15 days. It must be borne in mind that the components of the synthesis mixture may originate from different sources, which may modify the crystallisation conditions described.

According to a particular embodiment of the process of the present invention, it is possible to add AEI crystals to the synthesis mixture, which act as seeds that favour the synthesis described, in a quantity of up to 25% by weight with respect to the total quantity of oxides. These crystals may be added before or during the crystallisation process.

According to the process described, following the crystallisation described in (ii), the resulting solid is separated from the mother liquors and recovered. The recovery step (iii) may be performed by means of any well-known separation technique, such as, for example, decantation, filtration, ultrafiltration, centrifugation or any other solid-liquid separation technique, and combinations thereof.

The process of the present invention may further comprise the elimination of the organic content retained inside the material by means of an extraction process.

According to a particular embodiment, the elimination of the organic compound retained inside the material may be performed by means of a heat treatment at temperatures greater than 25° C., preferably between 100° C. and 1000° C., for a period of time preferably ranging between 2 minutes and 25 hours.

According to a particular embodiment of the present invention, in the process for obtaining the material described above, at least one metal may be further introduced by means of post-synthetic processes, such as impregnation, ion exchange or combinations thereof. These metals are preferably selected from precious metals and, more preferably, from Pt, Pd and combinations thereof, and they are preferably located at extra-lattice positions.

According to another particular embodiment of the present invention, during the process for obtaining the material described above, any metal oxide may be further introduced which contains, at least, one precious metal, preferably selected from Pt, Pd, and combinations thereof.

According to another particular embodiment, the material produced according to the present invention may be pelletised using any well-known technique.

According to a preferred embodiment, the material obtained according to the present invention may be calcined. Therefore, the zeolite material with the AEI structure may have the following molar composition after being calcined:

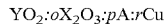

$YO_2:oX_2O_3:pA:rCu$ where o ranges between 0.001 and 0.2, preferably between 0.005 and 0.1, and, more preferably, between 0.01 and 0.07;

where p ranges between 0 and 2, preferably between 0.001 and 1, and, more preferably, between 0.01 and 0.8;

where r ranges between 0.001 and 1, preferably between 0.001 and 0.6, and, more preferably, between 0.001 and 0.5.

According to a particular embodiment, Y is Si and X is Al; therefore, the zeolite material with the AEI structure may present the following molar composition after being calcined:

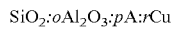

$SiO_2:oAl_2O_3:pA:rCu$ where o ranges between 0.001 and 0.2, preferably between 0.005 and 0.1, and, more preferably, between 0.01 and 0.07;

where p ranges between 0 and 2, preferably between 0.001 and 1, and, more preferably, between 0.01 a 0.8;

where r ranges between 0.001 and 1, preferably between 0.001 and 0.6, and, more preferably, between 0.001 and 0.5.

According to a preferred embodiment, the material obtained is Cu-SSZ-39.

According to a particular embodiment of the present invention, the zeolite material with the AEI structure obtained may further comprise a precious metal, preferably selected from Pd, Pt and combinations thereof.

The present invention also relates to the use of the materials described above, obtained according to the process of the present invention, as catalysts in the conversion of feeds formed by organic compounds into higher-added-value products, or as molecular sieves for the elimination/separation of streams (for example, gas mixtures), by placing the feeds in contact with the material obtained.

According to a preferred embodiment, the material obtained in the present invention may be used as a catalyst in the selective catalytic reduction (SCR) of NOx (nitrogen oxides) in a gas stream. In particular, the SCR of NOx will be performed in the presence of reducing agents, preferably selected from ammonium, urea, hydrocarbons, and combinations thereof. According to this particular embodiment, the selective catalytic reduction (SCR) of NOx (nitrogen oxides) may be performed using a monolith as the substrate, and applying a layer of the zeolite material obtained according to the present invention thereto, such that the gas stream may go through it to perform the desired reaction. Likewise, a layer of the zeolite material obtained according to the present invention may be applied to other substrates, such as, for example, a filter through which the gas stream may pass.

According to another particular embodiment of the present invention, the material synthesised according to the present invention, which contains a precious metal, such as Pt or Pd, may be used as a catalyst in the selective oxidation of ammonia to nitrogen. According to this particular embodiment, the selective catalytic oxidation of ammonia to nitrogen may be performed using a monolith as the substrate, and applying a layer of the zeolite material obtained according to the present invention thereto, such that the gas stream may go through it to perform the desired reaction. Likewise, a layer of the zeolite material obtained according to the present invention may be applied to other substrates, such as, for example, a filter, amongst others, through which the gas stream may pass.

According to another particular embodiment, the material described according to the present invention may be used in the conversion of methane into methanol (Wulfers, et al. Chem. Commun. 2015, 51, 4447).

Throughout the description and the claims, the word "comprises" and variants thereof are not intended to exclude other technical characteristics, additives, components or steps. For persons skilled in the art, other objects, advantages and characteristics of the invention will arise, partly from the description and partly from the practice of the invention.

EXAMPLES

Example 1: Synthesis of N,N-dimethyl-3,5-dimethylpiperidinium (DMDMP)

10 g of 3,5-dimethylpiperidine (Sigma-Aldrich, ≥96% by weight) is mixed with 19.51 g of potassium bicarbonate ($KHCO_3$, Sigma-Aldrich; 99.7% by weight), and dissolved in 140 ml of methanol. Subsequently, 54 ml of methyl iodide ($CH_3I$, Sigma-Aldrich, ≥99% by weight) is added, and the resulting mixture is kept under stirring for 5 days at room temperature. Once this time has elapsed, the reaction mixture is filtered in order to eliminate the potassium bicarbonate. The filtrated solution is partially concentrated by means of a rotary evaporator. Once the methanol has been partially evaporated, the solution is washed with chloroform several times and magnesium sulfate is added ($MgSO_4$, Sigma-Aldrich, ≥99.5% by weight). Subsequently, the mixture is filtered in order to eliminate the magnesium sulfate. The ammonium salt is obtained by precipitation with diethyl ether and subsequent filtration. The final yield of N,N-dimethyl-3,5-dimethylpiperidinium iodide is 85%.

In order to prepare the hydroxide form of the preceding organic salt: 10.13 g of the organic salt is dissolved in 75.3 g of water. Subsequently, 37.6 g of an anion-exchange resin (Dower SBR) is added, and the resulting mixture is kept under stirring for 24 hours. Finally, the solution is filtered, to obtain N,N-dimethyl-3,5-dimethylpiperidinium hydroxide (with a 94% exchange).

Example 2: Direct Synthesis of the Cu-Silicoaluminate with the AEI Structure 154.0 mg of a 20% by weight aqueous solution of copper sulfate (II) ($CuSO_4$, Alfa Aesar, 98%) is mixed with 31.2 mg of tetraethylenepentamine (TEPA, 98%, Sigma Aldrich), in order to prepare the organometallic copper-complex in situ, keeping the resulting mixture under stirring for 2 hours. Once this time has elapsed, 3216.0 mg of a 7.4% by weight aqueous solution of N,N-dimethyl-3,5-dimethylpiperidinium hydroxide and 163.1 mg of a 20% by weight aqueous solution of sodium hydroxide are added, keeping the resulting mixture under stirring for 15 minutes. Finally, 235.3 mg of a zeolite with the FAU structure (CBV-720, $SiO_2/Al_2O_3$ molar ratio=21) is introduced into the synthesis mixture and kept under stirring for the period of time required to evaporate the excess water and achieve the desired gel concentration. The final composition of the gel is $SiO_2$:0.047 $Al_2O_3$:0.046 $Cu(TEPA)^{2+}$:0.2 DMDMP:0.2 NaOH:23 $H_2O$. The resulting gel is transferred to a teflon-lined autoclave. The crystallisation is performed at 135° C. for 7 days under static conditions. The solid product is filtered, washed abundantly with water, dried at 100° C. and, finally, calcined in air at 550° C. for 4 h in order to eliminate the organic remainders. The yield of the solid obtained is greater than 90% (without taking the organic remainders into account).

Figure 1:
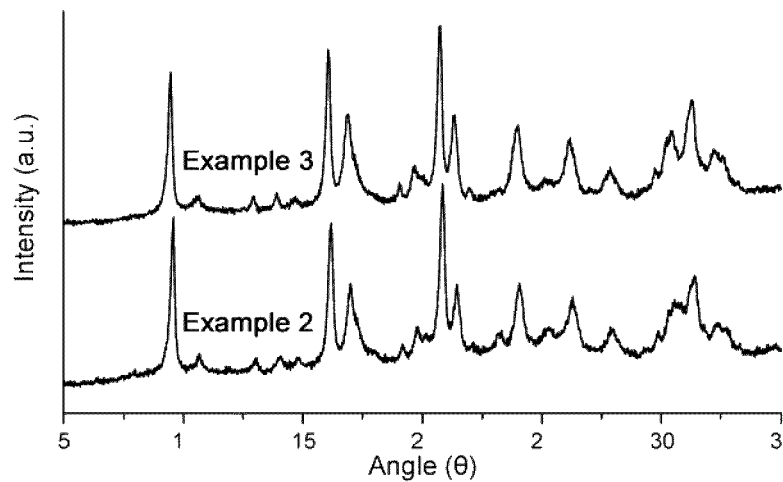
FIG. 1: PXRD patterns of the Cu-silicoaluminate materials with the AEI structure synthesised according to the present invention.

The solid is characterised by means of powder X-ray diffraction, and the characteristic peaks of the AEI structure are obtained (see FIG. 1). Chemical analyses of the sample indicate a Si/Al ratio of 9.95 and a copper content of 3.3% by weight.

Figure 2:
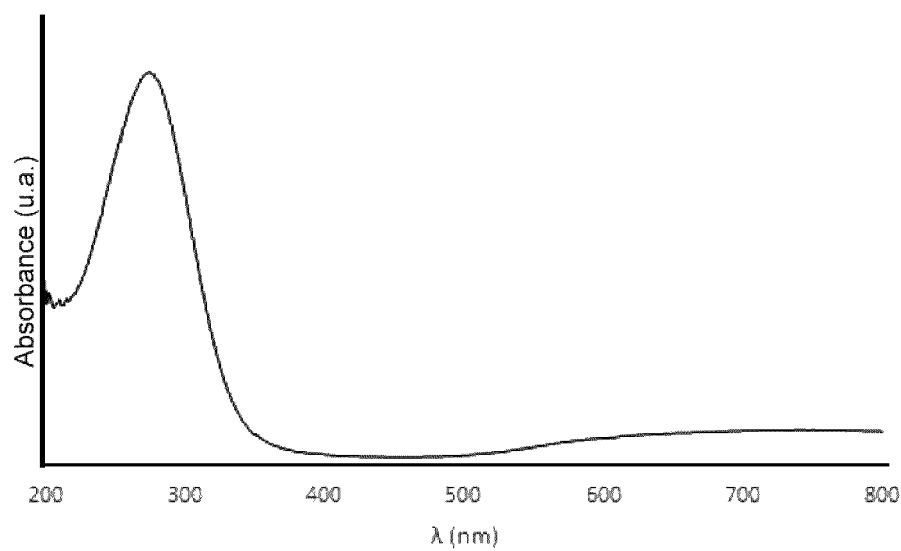
FIG. 2: UV-Vis spectrum of the Cu-silicoaluminate material with the AEI structure synthesised according to Example 2 of the present invention.

The uncalcined crystalline material obtained is characterised by UV-VIS spectroscopy in order to study the stability of the molecules of the organometallic copper-complex after the crystallisation of the zeolite. As can be observed in FIG. 2, the UV-VIS spectrum shows a single band centred at ~265 nm, which has been assigned to the presence of the intact Cu-TEPA complex inside the zeolite structure (Franco, et al. 2013/159828, 2012).

Example 3: Direct Synthesis of the Cu-Silicoaluminate with the AEI Structure 75.1 mg of a 20% by weight aqueous solution of copper sulfate (II) ($CuSO_4$, Alfa Aesar, 98%) is mixed with 18.0 mg of tetraethylenepentamine (TEPA, 98%, Sigma Aldrich), in order to prepare the organometallic copper-complex in situ, keeping the resulting mixture under stirring for 2 hours. Once this time has elapsed, 4049.0 mg of a 5.9% by weight aqueous solution of N,N-dimethyl-3,5-dimethylpiperidinium hydroxide and 159.1 mg of a 20% by weight aqueous solution of sodium hydroxide are added, keeping the resulting mixture under stirring for 15 minutes. Finally, 285.2 mg of a zeolite with the FAU structure (CBV-720, $SiO_2/Al_2O_3$ molar ratio=21) is introduced into the synthesis mixture, and kept under stirring for the period of time required to evaporate the excess water and achieve the desired gel concentration. The final composition of the gel is $SiO_2$:0.047 $Al_2O_3$:0.019 $Cu(TEPA)^{2+}$:0.3 DMDMP:0.2 NaOH:18 $H_2O$. The resulting gel is transferred to a teflon-lined autoclave. The crystallisation is performed at 135° C. for 7 days under static conditions. The solid product is filtered, washed abundantly with water, dried at 100° C. and, finally, calcined in air at 550° C. for 4 h in order to eliminate the organic remainders. The yield of the solid obtained is greater than 90% (without taking the organic remainders into account). The solid is characterised by means of powder X-ray diffraction, and the characteristic peaks of the AEI structure are obtained (see FIG. 1).

Example 4: Direct Synthesis of the Cu-Silicoaluminate with the AEI Structure 112.2 mg of a 20% by weight aqueous solution of copper sulfate (II) ($CuSO_4$, Alfa Aesar, 98%) is mixed with 27.0 mg of tetraethylenepentamine (TEPA, 98%, Sigma Aldrich), in order to prepare the organometallic copper-complex in situ, keeping the resulting mixture under stirring for 2 hours. Once this time has elapsed, 2416.0 mg of a 7.4% by weight aqueous solution of N,N-dimethyl-3,5-dimethylpiperidinium hydroxide and 66.2 mg of a 20% by weight aqueous solution of sodium hydroxide are added, keeping the resulting mixture under stirring for 15 minutes. Finally, 196.2 mg of a zeolite with the FAU structure (CBV-720, $SiO_2/Al_2O_3$ molar ratio=21) is introduced into the synthesis mixture, and kept under stirring for the period of time required to evaporate the excess water and achieve the desired gel concentration. The final composition of the gel is $SiO_2$:0.047 $Al_2O_3$:0.041 $Cu(TEPA)^{2+}$:0.3 DMDMP:0.1 NaOH:21 $H_2O$. The resulting gel is transferred to a teflon-lined autoclave. The crystallisation is performed at 135° C. for 7 days under static conditions. The solid product is filtered, washed abundantly with water, dried at 100° C. and, finally, calcined in air at 550° C. for 4 h in order to eliminate the organic remainders. The yield of the solid obtained is greater than 90% (without taking the organic remainders into account). The solid is characterised by means of powder X-ray diffraction, and the characteristic peaks of the AEI structure are obtained.

Example 5: Catalytic Assay of the SCR of $NO_x$

The catalytic activity for the selective catalytic reduction of NOx is studied using a quartz fixed-bed tubular reactor 1.2 cm in diameter and 20 cm in length. In a typical experiment, the catalyst is compacted into particles with a size ranging between 0.25-0.42 mm, which are introduced into the reactor, and the temperature is increased to 550° C. (see the reaction conditions in Table 1); subsequently, this temperature is maintained for one hour under a flow of nitrogen. Once the desired temperature has been reached, the reaction mixture is fed. The SCR of NOx is studied using $NH_3$ as the reducing agent. The NOx present at the reactor gas outlet is continuously analysed by means of a chemiluminescence detector (Thermo 62C). The catalytic results are summarised in Table 2.

TABLE 1

Reaction conditions for the SCR of NOx.

| | |
|---|---|
| Total gas flow (ml/min) | 300 |
| Catalyst loading (mg) | 40 |
| NO concentration (ppm) | 500 |
| $NH_3$ concentration (ppm) | 530 |

TABLE 1-continued

Reaction conditions for the SCR of NOx.

| | |
|---|---|
| $O_2$ concentration (%) | 7 |
| $H_2O$ concentration (%) | 5 |
| Temperature interval studied (° C.) | 170-550 |

TABLE 2

Conversion (%) of NOx at different temperatures (200, 250, 300, 350, 400, 450, 500) using the Cu-AEI catalyst synthesised following the methodology described in the present invention.
Conversion (%) of NOx at different temperatures

| | 200° C. | 250° C. | 300° C. | 350° C. | 400° C. | 450° C. | 500° C. |
|---|---|---|---|---|---|---|---|
| Example 2 | 71.7 | 98.4 | 99.6 | 99.8 | 97.1 | 96.9 | 85.1 |

The invention claimed is:

1. Process for the direct synthesis of a material with the copper-containing silicoaluminate form of the AEI zeolite structure, which comprises, at least, the following steps:
  (i) preparation of a mixture containing, at least,
    one source of water,
    one source of copper,
    one polyamine,
    one source of tetravalent element Y, one source of trivalent element X,
    one cyclic ammonium cation with alkyl substituents as the OSDA and
    one source of alkaline or alkaline-earth cations (A), where the synthesis mixture has the following molar composition:

    $YO_2:aX_2O_3:bOSDA:cA:dH_2O:eCu:f$ Polyamine where
    a ranges between 0.001 and 0.2;
    b ranges between 0.01 and 2;
    c ranges between 0 and 2;
    d ranges between 1 and 200;
    e ranges between 0.001 and 1; and
    f ranges between 0.001 and 1;
  (ii) crystallisation of the mixture obtained in (i) in a reactor; and
  (iii) recovery of the crystalline material obtained in (ii).

2. Process for the direct synthesis of a material according to claim 1, wherein c ranges between 0.001 and 1.

3. Process for the direct synthesis of a material according to claim 1, wherein Y is a tetravalent element selected from Si, Sn, Ti, Ge, and combinations thereof.

4. Process for the direct synthesis of a material according to claim 3, wherein Y is Si and originates from a source selected from silicon oxide, silicon halide, colloidal silica, fumed silica, tetraalkyl orthosilicate, silicate, silicic acid, a previously synthesised crystalline material, a previously synthesised amorphous material, and combinations thereof.

5. Process for the direct synthesis of a material according to claim 4, wherein the source of Y is a previously synthesised crystalline material.

6. Process for the direct synthesis of a material according to claim 1, wherein X is selected from Al, B, Fe, In, Ga, and combinations thereof.

7. Process for the direct synthesis of a material according to claim 6, wherein X is Al and originates from a source selected from aluminum salt, any hydrated aluminum oxide, any aluminum alkoxide, a previously synthesised crystalline material, a previously synthesised amorphous material and combinations thereof.

8. Process for the direct synthesis of a material according to claim 7, wherein the source of X is a previously synthesised crystalline material.

9. Process for the direct synthesis of a material according to claim 1, wherein a zeolite with the FAU structure is the only source of Y and X.

10. Process for the direct synthesis of a material according to claim 1, wherein any source of copper may be used in step (i).

11. Process for the direct synthesis of a material according to claim 10, wherein the source of copper is selected from nitrate, sulfate and oxalate salts, and combinations thereof.

12. Process for the direct synthesis of a material according to claim 1, wherein the cyclic ammonium cation used as the OSDA is a quaternary ammonium selected from N,N-dimethyl-3,5-dimethylpiperidinium (DMDMP), N,N-diethyl-2,6-dimethylpiperidinium (DEDMP), N,N-dimethyl-2,6-dimethylpiperidinium, N-ethyl-N-methyl-2,6-dimethylpiperidinium, and combinations thereof.

13. Process for the direct synthesis of a material according to claim 12, wherein the OSDA selected is N,N-dimethyl-3,5-dimethylpiperidinium.

14. Process for the direct synthesis of a material according to claim 1, wherein the polyamine of step (i) comprises primary amines, secondary amines, tertiary amines, or mixtures thereof.

15. Process for the direct synthesis of a material according to claim 14, wherein the polyamine required in step (i) is selected from tetraethylenepentamine, triethylenetetramine, 1,4,8,11-tetraazacyclotetradecane, 1,4,8,11-tetramethyl-1,4,8,11-tetraazacyclotetradecane, or mixtures thereof.

16. Process for the direct synthesis of a material according to claim 15, wherein the polyamine used in step (i) is tetraethylenepentamine.

17. Process for the direct synthesis of a material according to claim 1, wherein the crystallisation process described in (ii) is performed in autoclaves, under static or dynamic conditions.

18. Process for the direct synthesis of a material according to claim 1, wherein the crystallisation process described in (ii) is performed at a temperature ranging between 100° C. and 200° C.

19. Process for the direct synthesis of a material according to claim 1, wherein the crystallisation time for the process described in (ii) ranges between 6 hours and 50 days.

20. Process for the direct synthesis of a material according to claim 1, further comprising the addition of AEI crystals, as seeds, to the synthesis mixture in a quantity of up to 25% by weight with respect to the total quantity of oxides.

21. Process for the direct synthesis of a material according to claim 1, wherein the recovery step (iii) is performed by means of a separation technique selected from decantation, filtration, ultrafiltration, centrifugation, and combinations thereof.

22. Process for the direct synthesis of a material according to claim 1, further comprising the elimination of the organic content retained inside the material by an extraction process.

23. Process for the direct synthesis of a material according to claim 1, further comprising the elimination of the organic content retained inside the material by means of a heat treatment at temperatures ranging between 100° C. and 1000° C., for a period of time ranging between 2 minutes and 25 hours.

24. Process for the direct synthesis of a material according to claim 1, wherein the material obtained is pelletised.

25. Process for the direct synthesis of a material according to claim 1, further comprising the introduction of at least one precious metal.

26. Process for the direct synthesis of a material according to claim 25, wherein the precious metal is selected from Pd, Pt, and combinations thereof.

27. Process for the direct synthesis of a material with the copper-containing silicoaluminate form of the AEI zeolite structure, which comprises, at least, the following steps:
   (i) Preparation of a mixture containing, at least,
      one source of water,
      one source of copper,
      one polyamine, selected from tetraethylenepentamine, triethylenetetramine, 1,4,8,11-tetraazacyclotetradecane, 1,4,8,11-tetramethyl-1,4,8,11-tetraazacyclotetradecane, or mixtures thereof,
      one source of tetravalent element Y, which is Si, and one source of trivalent element X, which is Al, wherein a zeolite with the FAU structure is the only source of Y and X,
      one cyclic ammonium cation with alkyl substituents as the OSDA, selected from N,N-dimethyl-3,5-dimethylpiperidinium (DMDMP), N,N-diethyl-2,6-dimethylpiperidinium (DEDMP), N,N-dimethyl-2,6-dimethylpiperidinium, N-ethyl-N-methyl-2,6-dimethylpiperidinium and combinations thereof and
      one source of alkaline or alkaline-earth cations (A), selected from a source of Na, K, and combinations thereof, where the synthesis mixture has the following molar composition:

$YO_2{:}aX_2O_3{:}bOSDA{:}cA{:}dH_2O{:}eCu{:}f$ Polyamine where
   a ranges between 0.001 and 0.2;
   b ranges between 0.01 and 2;
   c ranges between 0.01 and 0.8;
   d ranges between 1 and 200;
   e ranges between 0.001 and 1;
   f ranges between 0.001 and 1;
   and wherein the molar ratio of $A{:}YO_2$ is at least 0.1,
wherein the mixture formed in (i) is free from any source of phosphorous,
wherein the mixture formed in (i) is free from any source of fluorine,
   (ii) Crystallisation of the mixture obtained in (i) in a reactor,
   (iii) Recovery of the crystalline material obtained in (ii).

28. Zeolite material with the AEI structure obtained according to the process described in claim 27, comprising the following molar composition after being calcined:

$YO_2{:}oX_2O_3{:}pA{:}rCu$ where o ranges between 0.001 and 0.2;
where p ranges between 0 and 2;
where r ranges between 0.001 and 1.

29. Zeolite material with the AEI structure obtained according to claim 28, wherein Y is Si and X is Al, and which has the following molar composition:

$SiO_2{:}oAl_2O_3{:}pA{:}rCu$ where o ranges between 0.001 and 0.2;
where p ranges between 0 and 2;
where r ranges between 0.001 and 1.

30. Zeolite material with the AEI structure obtained according to claim 28, wherein the material is a Cu-SSZ-39.

31. Zeolite material with the AEI structure obtained according to claim 28, further comprising a precious metal.

32. Zeolite material with the AEI structure obtained according to claim 31, wherein the precious metal is selected from Pd, Pt, and combinations thereof.

33. Method of using the zeolite material with the AEI structure according to claim 31, wherein the zeolite material is a catalyst in the selective oxidation of ammonia to nitrogen.

34. Method of using the zeolite material with the AEI structure described in claim 28, in processes for converting feeds formed by organic compounds into higher-value-added products, or for the elimination/separation of the reactive stream comprising the step of placing said feed in contact with the zeolite material.

35. Method of using the zeolite material with the AEI structure according to claim 34, wherein the zeolite material is a catalyst in the selective catalytic reduction (SCR) of nitrogen oxides (NOx) in a gas stream.

36. Method of using the zeolite material with the AEI structure according to claim 35, wherein the zeolite material is a catalyst in the SCR of NOx, which is performed in the presence of a reducing agent selected from ammonia, urea, hydrocarbons, and combinations thereof.

37. Method of using the zeolite material with the AEI structure according to claim 34, wherein the zeolite material is a catalyst in the conversion of methane into methanol.

* * * * *